United States Patent
Reitz et al.

(10) Patent No.: US 8,916,171 B2
(45) Date of Patent: Dec. 23, 2014

(54) TOPICAL DELIVERY OF VISCOUS MEDICATIONS FOR THE TREATMENT OF DISEASES ASSOCIATED WITH CHRONIC SINUSITIS

(75) Inventors: Russell N. Reitz, Camarillo, CA (US); Robert Scott Osbakken, Camarillo, CA (US)

(73) Assignee: Topical Sinus Therapeutics, Inc., Camarillo, CA (US)

( * ) Notice: Subject to any disclaimer, the term of this patent is extended or adjusted under 35 U.S.C. 154(b) by 265 days.

(21) Appl. No.: 13/095,227

(22) Filed: Apr. 27, 2011

(65) Prior Publication Data

US 2011/0275587 A1 Nov. 10, 2011

Related U.S. Application Data

(60) Provisional application No. 61/328,523, filed on Apr. 27, 2010.

(51) Int. Cl.
| | |
|---|---|
| A61K 45/06 | (2006.01) |
| A61K 31/573 | (2006.01) |
| A61K 9/06 | (2006.01) |
| A61K 9/00 | (2006.01) |
| A61K 31/7036 | (2006.01) |

(52) U.S. Cl.
CPC ............... *A61K 31/573* (2013.01); *A61K 45/06* (2013.01); *A61K 9/06* (2013.01); *A61K 9/0043* (2013.01); *A61K 31/7036* (2013.01)
USPC ....... 424/195.17; 424/744; 514/172; 514/458

(58) Field of Classification Search
USPC ...................... 424/195.17, 744; 514/172, 458
See application file for complete search history.

(56) References Cited

U.S. PATENT DOCUMENTS

| | | | |
|---|---|---|---|
| 3,035,971 A * | 5/1962 | Anderson ...................... 424/659 |
| 5,149,694 A | 9/1992 | Cagle et al. |
| 5,158,761 A * | 10/1992 | Kamishita et al. .............. 424/45 |
| 5,340,572 A * | 8/1994 | Patel et al. .................. 424/78.04 |
| 5,492,937 A | 2/1996 | Bogentoft et al. |
| 5,601,077 A * | 2/1997 | Imbert ...................... 128/200.14 |
| 5,876,709 A * | 3/1999 | Itoh et al. .................... 424/78.04 |
| 6,284,804 B1 | 9/2001 | Singh et al. |
| 6,835,536 B2 | 12/2004 | Krieger et al. |
| 7,544,192 B2 | 6/2009 | Eaton et al. |
| 7,686,798 B2 | 3/2010 | Eaton et al. |
| 2003/0059440 A1* | 3/2003 | Clarot et al. ............. 424/195.17 |
| 2005/0043706 A1 | 2/2005 | Eaton et al. |
| 2007/0099883 A1* | 5/2007 | Calis et al. ..................... 514/172 |
| 2007/0110788 A1 | 5/2007 | Hissong et al. |
| 2007/0129665 A1* | 6/2007 | Dickens et al. .................. 604/26 |
| 2007/0202149 A1 | 8/2007 | Faucher et al. |
| 2008/0058296 A1 | 3/2008 | Chaudry |
| 2008/0145322 A1 | 6/2008 | Eldridge |
| 2009/0017090 A1 | 1/2009 | Arensdorf et al. |
| 2010/0036000 A1 | 2/2010 | Lichter et al. |

FOREIGN PATENT DOCUMENTS

| | | |
|---|---|---|
| WO | WO 2004/082525 | 9/2004 |
| WO | WO 2008/089268 | 7/2008 |

OTHER PUBLICATIONS

S. Piskunov, "The Prolongation of Drug Action in the Treatment of Diseases of the Nose and Paranasal Sinuses," Rhinology, 31, (1993), pp. 33-36.

* cited by examiner

*Primary Examiner* — Ali Soroush
(74) *Attorney, Agent, or Firm* — Sheppard Mullin Richter & Hampton LLP

(57) ABSTRACT

A medication or combination of medications for the treatment of a disease involving the sinuses is incorporated into a sterile medical gel. The viscosity of the gel or the adhesion of the gel to the patient's sinus cavity allows the gel to be maintained in the cavity for a sufficient length of time for treatment of the affected area. This reduces the amount of wasted medication that would otherwise result from other topical methods.

14 Claims, No Drawings

TOPICAL DELIVERY OF VISCOUS MEDICATIONS FOR THE TREATMENT OF DISEASES ASSOCIATED WITH CHRONIC SINUSITIS

REFERENCE TO RELATED APPLICATIONS

This application claims priority to U.S. Provisional Patent Application No. 61/328,523 filed Apr. 27, 2010, which is incorporated herein by reference in its entirety.

TECHNICAL FIELD

The present invention relates generally to drug administration, and more particularly, some embodiments relate to viscous topical compositions for drug administration.

DESCRIPTION OF THE RELATED ART

Sinusitis is an inflammation of the paranasal sinuses. The problem with current treatments for chronic sinusitis is the delivery of medications in sufficient concentrations into the sinuses. The small sinus structures are hollow cavities with narrow openings where an infection may easily adhere to the lining of the sinuses and are difficult to reach. Oral medications (after absorption) and intravenous medications must pass from the blood stream into the sinus cavity(s) in effective concentrations and for a specific duration of time to fully eliminate the sinus infection. Often, using oral and intravenous drug therapy, it is extremely difficult to achieve drug concentration in the sinuses without causing side effects. With oral and intravenous therapy the absorbed drug travels to all areas of the body, this can negatively affect certain tissues, including other organs and organ systems.

There are numerous examples where a drug is metabolized in the liver only to be discontinued upon a rise in liver enzymes. In other cases, the kidneys are unable to timely remove the medication from the blood causing an increase in serum concentration over time. Increased serum concentration may lead to tissue and organ toxicities. Also, oral or intravenous administration of medication especially antibiotics, corticosteroids, or antifungals used to treat chronic sinusitis may lead to severe gastrointestinal side effects, resulting in premature discontinuation of the prescribed medication.

Typical treatments of sinus infection include the following methods of delivery (a) intravenous drug administration; (b) oral drug administration; (c) nasal sprays; (d) nebulization; (e) sinus irrigations or rinses; (f) pulsating irrigation; and (g) atomization.

Intravenous drug administration is usually very expensive. Depending on the prescribed drug and duration of therapy, a usual course of intravenous antibiotics/antifungals, etc could cost between $2,500.00 and $21,000 dollars. Also, the method requires drug management by monitoring of serum drug concentrations to prevent tissue/organ damage. Elevated serum levels of certain medications can lead to oto-toxicity (hearing loss) and renal tissue damage.

Oral drug administration often has gastrointestinal side effects, or lack of gastrointestinal absorption. Other organ system side effects include bone, tendon, or muscle pain. Oral drug administration can also result in insomnia and agitation.

Nasal sprays typically have a large particle size that can prevent penetration into the sinuses.

Nebulization often has lengthy treatment times, results in poor concentration of drug into the sinuses, and has possible pulmonary drug deposition.

Sinus irrigations or rinses suffer from poor compliance because they are not comfortable for patients. Moreover, studies indicate up to 97% of the medicated irrigation is wasted rushing out of the sinuses and nasal cavity. Furthermore, residual pockets of fluid may be a cause of more frequent infections. Pulsating irrigation devices suffer from the similar drug waste and residual fluid pockets as seen with sinus irrigations or rinses.

Atomizers provide a small volume of medication that may not penetrate into sinuses. In addition, short pulse atomization is often not sufficient in duration to penetrate or power into sinuses.

BRIEF SUMMARY OF EMBODIMENTS OF THE INVENTION

Embodiments of the present invention are directed towards viscous compositions for topical drug deliver into the sinuses.

One embodiment of the invention features a medicated gel, comprising: a sterile viscous fluid having a viscosity sufficient to be maintained within a human paranasal sinus cavity after insertion; and a medication dispersed in the sterile viscous fluid. In some cases, the sterile viscous fluid may have a viscosity between 2,000 centapoise and 128,000 centapoise at 20° C. In addition, the medication may comprise an anti-microbial medication, an antibiotic medication, an anti-inflammatory medication, an anti-fungal medication, a mucolytic medication, an antihistamine medication, a decongestant medication, a vasoconstrictor medication, an anti-viral medication, a chelating agent medication, or an oncologic medication. In some embodiments, the sterile viscous fluid comprises hydroxyethylcellulose, and the medication comprises tobramycin or mometasone. In further embodiments, the medication also comprises a micro fine Vitamin D3 suspension.

A further embodiment of the invention involves a medical kit, comprising a syringe and a medicated gel disposed within the syringe, wherein the medicated gel comprises a sterile viscous fluid having a viscosity sufficient to be maintained within a human paranasal sinus cavity after insertion and a medication dispersed in the sterile viscous fluid.

An additional embodiment of the invention involves a method of preparing a medicated gel, comprising: dissolving a medication in a solvent; forming a sterile gel; and dispersing the dissolved medication in the gel to form the medicated gel; wherein the medicated gel has a viscosity sufficient to be maintained within a human paranasal sinus cavity after insertion.

DESCRIPTION OF EMBODIMENTS OF THE INVENTION

The present invention is directed towards viscous compositions for topical drug deliver into the sinuses. Topically administered medications bypass many of the common side affects associated with medications that are administered orally or intravenously.

In one embodiment, a specific medication or combination of medications is incorporated into a medical gel. In a further embodiment, the gels comprise a specific medication or combination of medications in a water soluble formula. The viscosity of the gel or the adhesion of the gel to the patient's sinus cavity allows the gel to be maintained in the cavity for a sufficient length of time for treatment of the affected area. This reduces the amount of wasted medication that would otherwise result from other topical methods.

According to another embodiment, the medicated gel is applied via various surgical instruments known in the art directly onto and around the infected sinus anatomy. The route of application is through the nasal cavity. This direct application bypasses the requirement of sufficient blood/serum drug concentration over an extended period of time to treat the chronic sinus infection or related sinuses disease.

In some embodiments of the invention, a sterile gel that solvates a medication is provided for use in inserting the medication into the sinus cavities of a patient. In one embodiment, the gel comprises a mixture of hydroxyethylcellulose, water, and propylene glycol. In other embodiments, suitable gels may include biodegradable polymer gels, hydrogels, or other liquids having a suitable viscosity for maintaining the medicine in the sinus cavities of the patient. In some embodiments, such materials may include methylcellulose, carboxymethylcellulose, carbomer resins 690-941, hydroxypropyl-methylcellulose, hydroxypropyl cellulose and hypromellose.

In some embodiments, a medication is incorporated into the gel. Medications may include medications designed to treat various sinus related diseases, such as sinusitis, rhinitis, biofilm-caused diseases, or sinus polyps. In further embodiments, the gel and medication combination may be used as an aid in surgical procedures, such as surgical suction and surgical debridement. In these procedures, some gels embodiments, especially those containing an anti-inflammatory may be inserted immediately postoperatively to reduce tissue inflammation due to the surgical procedure and to promote tissue healing. Some embodiments, especially those containing an anti-inflammatory may be inserted directly into a sinus cavity containing polyps to reduce the size and possibly with repeated application eliminate the polyp's preventing a surgical procedure.

Medications used in various embodiments may include antimicrobial medications, antibiotic medications, anti-inflammatory medications, anti-fungal medications, mucolytic medications, antihistamine medications, decongestant medications, vasoconstrictor medications, anti-viral medications, chelating agent medications, oncologic medications, or combinations thereof. Some particular medications include mometasone, tobramycin, gentamicin, vancomycin, ceftriaxone, clindamycin, vancomycin, levofloxacin, ciprofloxacin, levofloxacin, and corticosteroids. Other medications include drugs within the following antibiotic drug classes: Penicillins; Cephalosporins; Tetracyclines; Macrolides; Quinolones; Fluoroquinolnes; Aminoglycosides; Carbapenems; Sulfonamides, and Polymixins. In further embodiments, the medications include drugs within the following anti-fungal (azoles) drug classes: Fluconazole, Itraconazole and Voriconazole. In still further embodiments, the medications include corticosteroid drugs such as, Mometasone, betamethasone, fluticasone, ciclesonide and budesonide. In further embodiments, the medications may include leukotriene receptor antagonists such as Montelukast and zafirlukast.

Additionally, some embodiments may include compounds or gel formulations that result in medication time release. Such compounds may include hypromellose and Liposomal soluble microspheres and including other lipid formulations and polymer compounds.

Example Preparation:

In an example embodiment, a medical gel comprises a 200 cc preparation of tobramycin/mometasone gel. Compounds used in making the gel include: (a.) 2000 mg of Tobramycin (10 mg/cc) (COA=0.676=2,959 mg); (b.) 48 mg of mometasone (1200 mcg/5 cc) (COA=1.0=48 mg); (c.) 6 g hydroxyethylcellulose; (d.) 25 cc of 100% ethyl alcohol; (e.) 12 cc propylene glycol; (f.) sterile water qs for 200 cc; and (g.) one drop per 200 cc final volume of polysorbate 80.

Preparation of the example gel is as follows:

Step 1. The measure amount of mometasone is dissolved in 25 cc ethyl alcohol 100%. The dissolved mometasone is drawn into a 20 cc sterile syringe with a 0.22 micron millipore disc filter attachment.

Step 2. The measure amount of tobramycin is dissolved in 15 cc of sterile water. The dissolved tobramycin is drawn into a 35 cc sterile syringe with a 0.22 micron millipore disc filter attachment.

Step 3. 150 cc of sterile water is measured and dispensed into a 300 cc glass beaker. The mixture is heated to boiling temperature. 12 cc of propylene glycol is added to the mixture. The temperature setting is maintained at 350° C. for 2 minutes.

Step 4. 6 g of hydroxyethylcellulose is added to the heated mixture of sterile water and propylene glycol. The mixture is stirred continuously while quickly adding the hydroxyethylcellulose. Once the addition of the hydroxyethylcellulose is complete; the mixture is stirred for one minute on the heat plate. During this step, the gel will begin to form.

Step 5. The mixture is removed from the heat plate. After removal from the heat plate, the gel will become more viscous. While stirring the mixture, the solution of ethyl alcohol/mometasone is slowly added. The gel will become opaque because the mometasone is insoluble in water. The mixture is returned to the heat plate and stirred for one minute. During this step, the ethyl alcohol will evaporate from the mixture.

Step 6. The mixture is removed from the heat plate. The mixture is continuously stirred while the mixture cools. When the gel cools, the dissolved tobramycin in sterile water solution is slowly added. Stirring continues for 5 minutes.

Step 7. While continuing to stir the medication gel, the entire beaker is placed into a bath of isopropyl alcohol 70% for two minutes to cool the gel.

Step 8. The medication gel is poured into a 60 cc syringe with a luer to luer connector, connecting the opposite end with a 12 cc luer tip syringe.

Step 9. Each 12 cc syringe is filled with 7 cc of gel. The filled syringes are kept in a vertical position. Any air bubbles will collect at the top of the syringe. After 5 minutes of cooling and in a vertical position, 1-2 cc of gel are decanted to remove the air, resulting in a final gel syringe volume of 5-6 cc. Using a sterile cap, the tip of the syringe is secured with the luer sterile cap.

Step 10. The gel filled syringes are stored refrigerated prior to shipping. Gel syringes are shipped under refrigerated conditions, for example with cool ice blocks. Upon arrival the gel is kept refrigerated.

Additionally, 24 and 48 hour inspections are suggested to inspect for suspended particulates. In one embodiment, using a syringe from the prepared lot, approximately 3 cc of gel are decanted at 48 hours to inspect for viscosity. This viscosity observation is further repeated at 72 hours.

In various embodiments, the viscosity requirements may vary according to factors such as physician preference, medication administered, patient, desired administration time, administration temperature, individual medications and medication diluents. Typical viscosities have the consistency of a petrolatum jelly preparation.

In one embodiment, the medicated gel may be introduced into the sinuses using a catheter, such as a suction catheter. In this embodiment, a syringe containing the gel is connected to the end of the catheter and the catheter is placed into the affected sinus cavity for gel insertion. The volume gel inserted into a given area depends on the extent of the sinus problem. In some embodiments, as little as 1 cc per affected area has been effective in treatment.

Further embodiments of the invention may feature compounds or gel formations that include Vitamin D3. Clinical literature illustrates that Vitamin D3 therapy has certain immunological benefits for patients suffering from chronic sinusitis with nasal polyps [CRSwNP] and patients diagnosed with allergic fungal rhinosinusitis [AFRS]. Chronic sinusitis patients with nasal polyps and allergic fungal sinusitis patients have been found to have insufficient levels of Vitamin D3. In addition, these patients were shown to have increased dendritic cells, which may play a part in the development of sinus tissue inflammation.

Increased Vitamin D3 has been shown in clinical studies to improve a cell's immunological response by lowering circulating dendritic cells in those patients with CRSwNP and AFRS. Immunological researchers have observed these and other benefits as it relates to sinus disease Vitamin D therapy has previously been topically administered inside an emollient base carrier for the purpose of alleviating inflammation and epithelial cell irritation. In addition, Vitamin D has been used in combination with other vitamins in various healthcare products such as ointments used in the care of diaper rash patients. One such combination includes Vitamin D and Vitamin A.

In an embodiment of the invention, a medical gel such as described above is modified to include Vitamin D3. In particular, the medical gel includes a micro fine Vitamin D3 suspension that is incorporated inside a hydrophilic carrier gel base. This Vitamin D3 hydrophilic gel may contain concentrations as low as 10 units per cc of Vitamin D3 and concentrations as high as 10,000 units per cc of Vitamin D3.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A medicated gel, comprising:
   a sterile viscous fluid having a viscosity sufficient to be maintained within a human paranasal sinus cavity after insertion; and
   a medication dispersed in the sterile viscous fluid;
   wherein the pH of the medicated gel is not adjusted by the addition of any acids, bases, or buffers, and the osmolality of the medicated gel is not adjusted by addition of any salts;
   wherein the sterile viscous fluid comprises hydroxyethylcellulose, and the medication comprises tobramycin or mometasone.

2. The medicated gel of claim 1, wherein the sterile viscous fluid has a viscosity between 2,000 centipoise and 128,000 centipoise at 20° C.

3. The medicated gel of claim 1, wherein the medication further comprises an antimicrobial medication, an antibiotic medication, an anti-inflammatory medication, an anti-fungal medication, a mucolytic medication, an antihistamine medication, a decongestant medication, a vasoconstrictor medication, an anti-viral medication, a chelating agent medication, or an oncologic medication.

4. The medicated gel of claim 1, wherein the medication further comprises a micro fine Vitamin D3 suspension.

5. A medical kit, comprising:
   a syringe; and a medicated gel disposed within the syringe;

wherein the medicated gel comprises a sterile viscous fluid having a viscosity sufficient to be maintained within a human paranasal sinus cavity after insertion and a medication dispersed in the sterile viscous fluid, the pH of the medicated gel is not adjusted by the addition of any acids, bases, or buffers, and the osmolality of the medicated gel is not adjusted by addition of any salts; and wherein the sterile viscous fluid comprises hydroxyethylcellulose, and the medication comprises tobramycin or mometasone.

6. The medical kit of claim 5, wherein the sterile viscous fluid has a viscosity between 2,000 centipoise and 128,000 centipoise at 20° C.

7. The medical kit of claim 5, wherein the medication further comprises an antimicrobial medication, an antibiotic medication, an anti-inflammatory medication, an anti-fungal medication, a mucolytic medication, an antihistamine medication, a decongestant medication, a vasoconstrictor medication, an anti-viral medication, a chelating agent medication, or an oncologic medication.

8. The medical kit of claim 5, wherein the medication further comprises a micro fine Vitamin D3 suspension.

9. A method of preparing a medicated gel, comprising:
dissolving a medication in a solvent;
forming a sterile gel; and
dispersing the dissolved medication in the gel to form the medicated gel;
wherein the medicated gel has a viscosity sufficient to be maintained within a human paranasal sinus cavity after insertion, the pH of the medicated gel is not adjusted by the addition of any acids, bases, or buffers, and the osmolality of the medicated gel is not adjusted by addition of any salts;
wherein the solvent comprises water or propylene glycol, and the medication comprises tobramycin or mometasone.

10. The method of claim 9, wherein the medication further comprises a micro fine Vitamin D3 suspension.

11. A medicated gel, comprising:
a sterile viscous fluid having a viscosity sufficient to be maintained within a human paranasal sinus cavity after insertion; and
a medication dispersed in the sterile viscous fluid, wherein the sterile viscous fluid has a viscosity between 2,000 centipoise and 128,000 centipoise at 20° C.,
wherein the medication comprises an antimicrobial medication, an antibiotic medication, an anti-inflammatory medication, an anti-fungal medication, a mucolytic medication, an antihistamine medication, a decongestant medication, a vasoconstrictor medication, an anti-viral medication, a chelating agent medication, or an oncologic medication, wherein the sterile viscous fluid comprise hydroxyethylcellulose, and the medication comprises tobramycin or mometasone, and wherein the medication further comprises a micro fine Vitamin D3 suspension; and wherein the pH of the medicated gel is not adjusted by the addition of any acids, bases, or buffers, and the osmolality of the medicated gel is not adjusted by addition of any salts.

12. A medicated gel, consisting essentially of:
a sterile viscous fluid having a viscosity sufficient to be maintained within a human paranasal sinus cavity after insertion; and
a medication dispersed in the sterile viscous fluid;
wherein the sterile viscous fluid comprises hydroxyethylcellulose, and the medication comprises tobramycin or mometasone.

13. A medical kit, comprising:
a syringe; and
a medicated gel disposed within the syringe;
wherein the medicated gel consists essentially of a sterile viscous fluid having a viscosity sufficient to be maintained within a human paranasal sinus cavity after insertion and a medication dispersed in the sterile viscous fluid;
wherein the sterile viscous fluid comprise hydroxyethylcellulose, and the medication comprises tobramycin or mometasone.

14. A method of preparing a medicated gel, consisting essentially of:
dissolving a medication in a solvent;
forming a sterile gel; and
dispersing the dissolved medication in the gel to form the medicated gel;
wherein the medicated gel has a viscosity sufficient to be maintained within a human paranasal sinus cavity after insertion;
wherein the solvent comprises water or propylene glycol, and the medication comprises tobramycin or mometasone.

* * * * *